US008133251B2

(12) United States Patent
Ravenscroft et al.

(10) Patent No.: US 8,133,251 B2
(45) Date of Patent: *Mar. 13, 2012

(54) REMOVEABLE EMBOLUS BLOOD CLOT FILTER AND FILTER DELIVERY UNIT

(75) Inventors: Adrian C. Ravenscroft, Milton, MA (US); Stephen J. Kleshinski, Scituate, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 1682 days.

This patent is subject to a terminal disclaimer.

(21) Appl. No.: 11/150,661

(22) Filed: Jun. 10, 2005

(65) Prior Publication Data

US 2005/0234503 A1 Oct. 20, 2005

Related U.S. Application Data

(60) Continuation of application No. 09/640,865, filed on Aug. 18, 2000, now Pat. No. 7,314,477, which is a division of application No. 09/360,654, filed on Jul. 26, 1999, now Pat. No. 6,258,026, which is a continuation-in-part of application No. 09/160,384, filed on Sep. 25, 1998, now Pat. No. 6,007,558.

(51) Int. Cl.
*A61F 2/06* (2006.01)
*A61M 29/00* (2006.01)
(52) U.S. Cl. ........ 606/200; 606/191; 606/194; 606/195; 606/198; 604/94; 604/95; 604/96; 604/164; 623/1.11
(58) Field of Classification Search .......... 606/191–200; 623/1.11; 604/94–96, 164
See application file for complete search history.

(56) References Cited

U.S. PATENT DOCUMENTS

| 2,767,703 A | 10/1956 | Nieburgs |
| 3,472,230 A | 10/1969 | Fogarty |
| 3,540,431 A | 11/1970 | Mobin-Uddin |

(Continued)

FOREIGN PATENT DOCUMENTS

DE 36 33 527 A1 4/1988

(Continued)

OTHER PUBLICATIONS

Cook, "Gunther Tulip Vena Cava Mreye™ Filter" Sales Brochure (2001).

(Continued)

*Primary Examiner* — Vy Q Bui
(74) *Attorney, Agent, or Firm* — Rutan & Tucker, LLP

(57) ABSTRACT

A blood clot filter which is collapsible toward a central longitudinal axis into a collapsed configuration for insertion into a blood vessel and which is radially expandable outwardly from the longitudinal axis to an expanded configuration for contact with the inner wall of the blood vessel at two longitudinal spaced locations. A first plurality of spaced, elongate arms, in the expanded configuration of the filter, curve outwardly away from the longitudinal axis toward the leading end of the filter to form a first filter basket and to center a hub at the trailing end of the filter within the vessel. A second plurality of spaced elongate legs angle outwardly away from the longitudinal axis toward the leading edge of the filter in the expanded configuration thereof to form a second filter basket opening toward the leading end. The ends of these legs include hooks to bend and straighten in response to withdrawal force.

3 Claims, 3 Drawing Sheets

U.S. PATENT DOCUMENTS

| | | | |
|---|---|---|---|
| 3,579,798 A | 5/1971 | Henderson | |
| 3,620,212 A | 11/1971 | Fannon, Jr. et al. | |
| 3,952,747 A | 4/1976 | Kimmell, Jr. | |
| 4,198,960 A | 4/1980 | Utsugi | |
| 4,425,908 A | 1/1984 | Simon | |
| 4,494,531 A | 1/1985 | Gianturco | |
| 4,586,501 A | 5/1986 | Claracq | |
| 4,611,594 A | 9/1986 | Grayhack et al. | |
| 4,619,246 A | 10/1986 | Molgaard-Nielsen et al. | |
| 4,643,184 A | 2/1987 | Mobin-Uddin | |
| 4,655,219 A | 4/1987 | Petruzzi | |
| 4,665,906 A | 5/1987 | Jervis | |
| 4,680,573 A | 7/1987 | Ciordinik et al. | |
| 4,688,553 A * | 8/1987 | Metals ............... | 128/899 |
| 4,727,873 A | 3/1988 | Mobin-Uddin | |
| 4,781,177 A | 11/1988 | Lebigot | |
| 4,793,348 A | 12/1988 | Palmaz | |
| 4,817,600 A | 4/1989 | Herms et al. | |
| 4,832,055 A | 5/1989 | Palestrant | |
| 4,957,501 A | 9/1990 | Lahille et al. | |
| 4,969,891 A | 11/1990 | Gewertz | |
| 4,990,151 A | 2/1991 | Wallsten | |
| 4,990,156 A | 2/1991 | Lefebvre | |
| 5,059,205 A | 10/1991 | El-Nounou et al. | |
| 5,067,957 A | 11/1991 | Jervis | |
| 5,074,867 A | 12/1991 | Wilk | |
| 5,098,440 A | 3/1992 | Hillstead | |
| 5,108,418 A | 4/1992 | Lefebvre | |
| 5,120,308 A | 6/1992 | Hess | |
| 5,133,733 A | 7/1992 | Rasmussen et al. | |
| 5,147,378 A | 9/1992 | Markham | |
| 5,147,379 A | 9/1992 | Sabbaghian et al. | |
| 5,152,777 A | 10/1992 | Goldberg et al. | |
| 5,190,546 A | 3/1993 | Jervis | |
| 5,219,358 A | 6/1993 | Bendel et al. | |
| 5,242,462 A | 9/1993 | El-Nounou et al. | |
| 5,324,304 A | 6/1994 | Rasmussen | |
| 5,329,942 A | 7/1994 | Gunther et al. | |
| 5,350,398 A | 9/1994 | Pavenik et al. | |
| 5,370,657 A | 12/1994 | Irie | |
| 5,375,612 A | 12/1994 | Cottenceau et al. | |
| 5,383,887 A | 1/1995 | Nadal | |
| 5,413,586 A | 5/1995 | Dibie et al. | |
| 5,423,851 A | 6/1995 | Samuels | |
| 5,464,408 A | 11/1995 | Duc | |
| 5,531,788 A | 7/1996 | Dibie et al. | |
| 5,545,210 A | 8/1996 | Hess et al. | |
| 5,549,626 A | 8/1996 | Miller et al. | |
| 5,554,181 A | 9/1996 | Das | |
| 5,597,378 A | 1/1997 | Jervis | |
| 5,601,595 A | 2/1997 | Smith | |
| 5,626,605 A | 5/1997 | Irie et al. | |
| 5,630,822 A | 5/1997 | Hermann et al. | |
| 5,634,942 A | 6/1997 | Chevillon et al. | |
| 5,649,906 A | 7/1997 | Gory et al. | |
| 5,669,933 A | 9/1997 | Simon et al. | |
| 5,683,411 A | 11/1997 | Kavteladze et al. | |
| 5,695,518 A | 12/1997 | Laerum | |
| 5,704,910 A | 1/1998 | Humes | |
| 5,709,704 A | 1/1998 | Nott et al. | |
| 5,720,764 A | 2/1998 | Naderlinger | |
| 5,746,767 A | 5/1998 | Smith | |
| 5,755,790 A | 5/1998 | Chevillon et al. | |
| 5,776,162 A | 7/1998 | Kleshinski | |
| 5,776,181 A | 7/1998 | Lee et al. | |
| 5,800,457 A | 9/1998 | Gelbfish | |
| 5,836,968 A * | 11/1998 | Simon et al. .......... | 606/200 |
| 5,836,969 A | 11/1998 | Kim et al. | |
| 5,853,420 A | 12/1998 | Chevillon et al. | |
| 5,893,869 A | 4/1999 | Barnhart et al. | |
| 5,911,704 A | 6/1999 | Humes | |
| 5,919,224 A | 7/1999 | Thompson et al. | |
| 5,928,261 A | 7/1999 | Ruiz | |
| 5,944,728 A | 8/1999 | Bates | |
| 5,954,741 A | 9/1999 | Fox | |
| 5,984,947 A | 11/1999 | Smith | |
| 5,989,266 A | 11/1999 | Foster | |
| 6,007,558 A | 12/1999 | Ravenscroft et al. | |
| 6,013,093 A | 1/2000 | Nott et al. | |
| 6,059,825 A | 5/2000 | Hobbs et al. | |
| 6,080,178 A | 6/2000 | Meglin | |
| 6,099,534 A | 8/2000 | Bates et al. | |
| 6,126,673 A | 10/2000 | Kim et al. | |
| 6,146,404 A | 11/2000 | Kim et al. | |
| 6,156,055 A | 12/2000 | Ravenscroft | |
| 6,193,739 B1 | 2/2001 | Chevillon et al. | |
| 6,193,748 B1 | 2/2001 | Thompson et al. | |
| 6,214,025 B1 | 4/2001 | Thistle et al. | |
| 6,217,600 B1 | 4/2001 | DiMatteo | |
| 6,231,581 B1 | 5/2001 | Shank et al. | |
| 6,231,589 B1 | 5/2001 | Wessman et al. | |
| 6,241,738 B1 | 6/2001 | Dereume | |
| 6,241,746 B1 | 6/2001 | Bosma et al. | |
| 6,245,012 B1 | 6/2001 | Kleshinski | |
| 6,251,122 B1 | 6/2001 | Tsukernik | |
| 6,258,026 B1 | 7/2001 | Ravenscroft et al. | |
| 6,264,664 B1 | 7/2001 | Avellanet | |
| 6,267,776 B1 | 7/2001 | O'Connell | |
| 6,267,777 B1 | 7/2001 | Bosma et al. | |
| 6,273,900 B1 | 8/2001 | Nott et al. | |
| 6,273,901 B1 | 8/2001 | Whitcher et al. | |
| 6,280,451 B1 | 8/2001 | Bates et al. | |
| 6,280,459 B1 | 8/2001 | Doble | |
| 6,287,332 B1 | 9/2001 | Bolz et al. | |
| 6,383,193 B1 | 5/2002 | Cathcart et al. | |
| 6,383,206 B1 | 5/2002 | Gillick et al. | |
| 6,391,045 B1 | 5/2002 | Kim et al. | |
| 6,436,120 B1 | 8/2002 | Meglin | |
| 6,436,121 B1 | 8/2002 | Blom | |
| 6,443,972 B1 | 9/2002 | Bosma et al. | |
| 6,447,530 B1 | 9/2002 | Ostrovsky et al. | |
| 6,468,290 B1 | 10/2002 | Weldon et al. | |
| 6,482,222 B1 | 11/2002 | Bruckheimer et al. | |
| 6,485,502 B2 | 11/2002 | Don Michael et al. | |
| 6,497,709 B1 | 12/2002 | Heath | |
| 6,506,205 B2 | 1/2003 | Goldberg et al. | |
| 6,517,559 B1 | 2/2003 | O'Connell | |
| 6,517,573 B1 | 2/2003 | Pollock et al. | |
| 6,540,767 B1 | 4/2003 | Walak et al. | |
| 6,551,340 B1 | 4/2003 | Kónya et al. | |
| 6,558,406 B2 | 5/2003 | Okada | |
| 6,569,183 B1 | 5/2003 | Kim et al. | |
| 6,572,605 B1 | 6/2003 | Humes | |
| 6,582,447 B1 | 6/2003 | Patel et al. | |
| 6,589,266 B2 | 7/2003 | Whitcher et al. | |
| 6,620,183 B2 | 9/2003 | DiMatteo | |
| 6,623,506 B2 | 9/2003 | McGuckin, Jr. et al. | |
| 6,645,224 B2 | 11/2003 | Gilson et al. | |
| 6,652,558 B2 | 11/2003 | Patel et al. | |
| 6,685,738 B2 | 2/2004 | Chouinard et al. | |
| 6,702,834 B1 | 3/2004 | Boylan et al. | |
| 6,706,054 B2 | 3/2004 | Wessman et al. | |
| 6,843,798 B2 | 1/2005 | Kusleika et al. | |
| 6,989,021 B2 | 1/2006 | Bosma et al. | |
| 7,314,477 B1 | 1/2008 | Ravenscroft et al. | |
| 7,338,512 B2 | 3/2008 | McGuckin, Jr. et al. | |
| 7,544,202 B2 | 6/2009 | Cartier et al. | |
| 7,625,390 B2 | 12/2009 | Hendriksen et al. | |
| 7,699,867 B2 | 4/2010 | Hendriksen et al. | |
| 7,704,267 B2 | 4/2010 | Tessmer | |
| 2001/0000799 A1 | 5/2001 | Wessman et al. | |
| 2002/0032461 A1 | 3/2002 | Marshall | |
| 2002/0138097 A1 | 9/2002 | Ostrovsky et al. | |
| 2002/0193828 A1 | 12/2002 | Griffin et al. | |
| 2003/0004540 A1 | 1/2003 | Linder et al. | |
| 2003/0004541 A1 | 1/2003 | Linder et al. | |
| 2003/0004946 A1 | 1/2003 | VanDenAvond et al. | |
| 2003/0055812 A1 | 3/2003 | Williams et al. | |
| 2003/0114735 A1 | 6/2003 | Silver et al. | |
| 2003/0130680 A1 | 7/2003 | Russell | |
| 2003/0176888 A1 | 9/2003 | O'Connell | |
| 2003/0208227 A1 | 11/2003 | Thomas | |
| 2004/0073252 A1 | 4/2004 | Goldberg et al. | |
| 2004/0082966 A1 | 4/2004 | WasDyke | |
| 2004/0087999 A1 | 5/2004 | Bosma et al. | |
| 2004/0088000 A1 | 5/2004 | Muller | |
| 2004/0088001 A1 | 5/2004 | Bosma et al. | |

| | | | |
|---|---|---|---|
| 2004/0088002 A1 | 5/2004 | Boyle et al. | |
| 2004/0093015 A1 | 5/2004 | Ogle | |
| 2004/0116959 A1 | 6/2004 | McGuckin, Jr. et al. | |
| 2004/0138693 A1 | 7/2004 | Eskuri et al. | |
| 2004/0153110 A1 | 8/2004 | Kurz et al. | |
| 2004/0153118 A1 | 8/2004 | Clubb et al. | |
| 2004/0153119 A1 | 8/2004 | Kusleika et al. | |
| 2004/0158274 A1 | 8/2004 | WasDyke | |
| 2004/0167568 A1 | 8/2004 | Boyle et al. | |
| 2004/0176672 A1 | 9/2004 | Silver et al. | |
| 2004/0193209 A1 | 9/2004 | Pavenik et al. | |
| 2004/0220611 A1 | 11/2004 | Ogle | |
| 2004/0230220 A1 | 11/2004 | Osborne | |
| 2005/0021152 A1 | 1/2005 | Ogle et al. | |
| 2005/0055045 A1 | 3/2005 | DeVries et al. | |
| 2005/0055046 A1 | 3/2005 | McGuckin, Jr. et al. | |
| 2005/0080449 A1 | 4/2005 | Mulder | |
| 2005/0085847 A1 | 4/2005 | Galdonik et al. | |
| 2006/0106417 A1 | 5/2006 | Tessmer et al. | |
| 2007/0112373 A1 | 5/2007 | Carr et al. | |
| 2007/0167974 A1 | 7/2007 | Cully et al. | |
| 2007/0198050 A1 | 8/2007 | Ravenscroft et al. | |
| 2008/0039891 A1 | 2/2008 | McGuckin et al. | |
| 2009/0131970 A1 | 5/2009 | Chanduszko et al. | |
| 2009/0318951 A1 | 12/2009 | Kashkarov et al. | |

FOREIGN PATENT DOCUMENTS

| | | |
|---|---|---|
| EP | 0145166 A2 | 6/1985 |
| EP | 0188927 A2 | 7/1986 |
| FR | 2567405 A1 | 1/1986 |
| FR | 2718950 A1 | 10/1995 |
| SV | 07A000025 | 4/1997 |
| WO | WO95/09567 | 4/1995 |
| WO | 9612448 A1 | 5/1996 |
| WO | 9617634 A2 | 6/1996 |
| WO | 9802203 A1 | 1/1998 |
| WO | 9823322 A1 | 6/1998 |
| WO | 9925252 A1 | 5/1999 |
| WO | 0012011 A1 | 3/2000 |
| WO | 0018467 A1 | 4/2000 |
| WO | WO00/56390 | 9/2000 |
| WO | 0076422 A1 | 12/2000 |
| WO | 0204060 A1 | 1/2002 |
| WO | 2004098459 A1 | 11/2004 |
| WO | 2004098460 A1 | 11/2004 |
| WO | 2005072645 A1 | 8/2005 |
| WO | 2005102437 A2 | 11/2005 |
| WO | 2005102439 A2 | 11/2005 |
| WO | 2006036457 A2 | 4/2006 |
| WO | 2006124405 A2 | 11/2006 |
| WO | 2007021340 A1 | 2/2007 |
| WO | 2007100619 A2 | 9/2007 |
| WO | 2007106378 A2 | 9/2007 |

OTHER PUBLICATIONS

Cook, "Bird's Nest", *Vena Cava Filter*, Cook Incorporated, a Cook Group Company (Nov. 1982).
Cynamon et al., "Percutaneous Removal of a Titanium Greenfield Filter" *AJR* 159:777-778 (Oct. 1992).
Dotter et al., "Transluminal Expandable Nitinol Coil Stent Grafting: Preliminary Report" *Radiology* 147:259-260 (Apr. 1983).
Engmann and Asch, "Clinical Experience with the Antecubital Simon Nitinol IVC Filter" *JVIR* 9:774-778 (1998).
Epstein et al., "Experience with the Amplatz Retrievable Vena Cava Filter" *Radiology* 175:105-110 (1989).
Greenfield et al., "Results of a Multicenter Study of the Modified Hook-Titanium Greenfield Filter" *Journal of Vascular Surgery* 14:253-257 (Sep. 1991).
Hansen, "Metals that Remember" *Science* 81:44-47, date unknown.
Kim et al., "Insertion of the Simon Nitinol Caval Filter: Value of the Antecubital Vein Approach" *AJR* 157:521-522 (Sep. 1991).
Kim et al., "Perforation of the Inferior Vena Cava with Aortic and Vertebral Penetration by a Suprarenal Greenfield Filter" *Radiology* 172:721-723 (1989).
Kim et al., "Vena Cava Filter Placement Via the External Jugular Vein" *AJR* 155:898-899 (Oct. 1990).
Kim et al., "The Simon Nitinol Filter: Evaluation by MR and Ultrasound" *Angiology* 43:541-548 (Jul. 1992).
Malden et al., "Transvenous Retrieval of Misplaced Stainless Steel Greenfield Filters" *JVIR* 3:703-708 (1992).
McCowan et al., "Complications of the Nitinol Vena Cava Filter" *JVIR* 3:401-408 (1992).
Millward, "Temporary and Retrievable Inferior Vena Cava Filters: Current Status" *JVIR* 9:381-387 (1998).
Nakagawa et al., "A Retrievable Nitinol Vena Cava Filter: Experimental and Initial Clinical Results" *JVIR* 5:507-512 (1994).
Neuerburg et al., "New Retrievable Percutaneous Vena Cava Filter: Expermental In Vitro and In Vivo Evaluation" *Cardiovasc. Intervent. Radiol.*16:224-229 (1993).
Palastrant et al., "Comparative In Vitro Evaluation of the Nitinol Inferior Vena Cava Filter" *Radiology* 145:351-355 (Nov. 1982).
Prince et al., "Local Intravascular Effects of the Nitinol Wire Blood Clot Filter" *Investigative Radiology* 23:294-300 (Apr. 1988).
Prince et al., "The Diameter of the Inferior Vena Cava and Its Implications for the Use of Vena Cava Filters" *Radiology* 149:687-689 (1983).
Putnam et al., "Placement of Bilateral Simon Nitinol Filters for an Inferior Vena Cava Duplication through a Single Groin Access" *JVIR* 10:431-433 (1999).
Qian et al., "In Vitro and In Vivo Experimental Evaluation of a New Vena Cava Filter" *JVIR* 5:513-518 (1994).
Salamipour et al., "Percutaneous Transfemoral Retrieval of a Partially Deployed Simon-Nitinol Filter Misplaced into the Ascending Lumbar Vein" *JVIR* 7:917-919 (1996).
Sequeira et al., "A Safe Technique for Introduction of the Kimray-Greenfield Filter" *Radiology* 133:799-800 (Dec. 1979).
Siegel and Robertson, "Percutaneous Tranfemoral Retrieval of a Free-Floating Titanium Greenfield Filter with an Amplatz Goose Neck Snare" *JVIR* 4:565-568 (1993).
Simon et al., "A Vena Cava Filter Using Thermal Shape Memory Alloy" *Radiology* 125:89-94 (Oct. 1977).
Simon et al., "Simon Nitinol Inferior Vena Cava Filter: Initial Clinical Experience" *Radiology* 172:99-103 (1989).
Simon et al., "Transvenous Devices for the Management of Pulmonary Embolism" *Cardiovascular and Interventional Radiology* 3:308-313, 112-120 (1980).
Simon, "Vena Cava Filters: Prevalent Misconceptions" *JVIR* 10:1021-1024 (1999).
Vesley et al., "Preliminary Investigation of the Irie Inferior Vena Cava Filter" *JVIR* 7:529-535 (1996).
Zwaan et al., "Clinical Experience with Temporary Vena Cava Filters" *JVIR* 9:594-601 (1998).
C.R. Bard Simon Nitinol Filter: For Use in the Vena Cava: Instructions for Use (1995, 1997).
U.S. Appl. No. 11/997,832, filed Aug. 20, 2008 Non-Final Office Action dated Aug. 16, 2010.
PCT/US1999/020883 filed Sep. 23, 1999 Search Report dated Jan. 20, 2000.
PCT/US2006/017890 filed May 9, 2006 Preliminary Report on Patentability dated Feb. 12, 2008.
PCT/US2006/017890 filed May 9, 2006 Search Report dated Nov. 2, 2006.
PCT/US2006/017890 filed May 9, 2006 Written Opinion dated Nov. 2, 2006.

* cited by examiner

REMOVEABLE EMBOLUS BLOOD CLOT FILTER AND FILTER DELIVERY UNIT

PRIORITY

This application is a continuation of U.S. patent application Ser. No. 09/640,865, filed on Aug. 18, 2000, now U.S. Pat. No. 7,314,477, which is a division of U.S. patent application Ser. No. 09/360,654, filed on Jul. 26, 1999, now U.S. Pat. No. 6,258,026, which is a continuation-in-part of U.S. patent application Ser. No. 09/160,384, filed on Sep. 25, 1998, now U.S. Pat. No. 6,007,558. Each of the previously mentioned applications and patents is incorporated by reference in its entirety into this application.

BACKGROUND OF THE INVENTION

In recent years, a number of medical devices have been designed which are adapted for compression into a small size to facilitate introduction into a vascular passageway and which are subsequently expandable into contact with the walls of the passageway. These devices, among others, include blood clot filters which expand and are held in position by engagement with the inner wall of a vein. It has been found to be advantageous to form such devices of a shape memory material having a first, relatively pliable low temperature condition and a second, relatively rigid high-temperature condition. By forming such devices of temperature responsive material, the device in a flexible and reduced stress state may be compressed and fit within the bore of a delivery catheter when exposed to a temperature below a predetermined transition temperature, but at temperatures at or above the transition temperature, the device expands and becomes relatively rigid.

Known self expanding medical devices have been formed of Nitinol, an alloy of titanium and nickel which provides the device with a thermal memory. The unique characteristic of this alloy is its thermally triggered shape memory, which allows a device constructed of the alloy to be cooled below a temperature transformation level to a martensitic state and thereby softened for loading into a catheter in a relatively compressed and elongated state, and to regain the memorized shape in an austenitic state when warmed to a selected temperature above the temperature transformation level, such as human body temperature. The two interchangeable shapes are possible because of the two distinct microcrystalline structures that are interchangeable with a small variation in temperature. The temperature at which the device assumes its first configuration may be varied within wide limits by changing the composition of the alloy. Thus, while for human use the alloy may be focused on a transition temperature range close to 98.6.degree. F., the alloy readily may be modified for use in animals with different body temperatures.

U.S. Pat. No. 4,425,908 to Simon discloses a very effective blood clot filter formed of thermal shape memory material. This filter, like most previously developed vena cava filters such as those also shown by U.S. Pat. Nos. 5,108,418 to Lefebvre, 5,133,733 to Rasmussen et al., 5,242,462 to El-Nounou et al., 5,800,457 to Gelbfish and 5,853,420 to Chevillon et al. is a permanent filter which, when once implanted, is designed to remain in place. Such filters include structure to anchor the filter in place within the vena cava, such as elongate diverging legs with hooked ends that penetrate the vessel wall and positively prevent migration in either direction longitudinally of the vessel. The hooks on filters of this type are rigid and will not bend, and within two to six weeks after a filter of this type has been implanted, the endothelium layer grows over the diverging legs and positively locks the hooks in place. Now any attempt to remove the filter results in a risk of injury to or rupture of the vena cava.

A number of medical procedures subject the patient to a short term risk of pulmonary embolism which can be alleviated by a filter implant. In such cases, patients are often adverse to receiving a permanent implant, for the risk of pulmonary embolism may disappear after a period of several weeks or months. However, most existing filters are not easily or safely removable after they have remained in place for more than two weeks, and consequently longer term temporary filters which do not result in the likelihood of injury to the vessel wall upon removal are not available.

In an attempt to provide a removable filter, two filter baskets have been formed along a central shaft which are conical in configuration, with each basket being formed by spaced struts radiating outwardly from a central hub for the basket. The central hubs are held apart by a compression unit, and the arms of the two baskets overlap so that the baskets face one another. Devices of this type require the use of two removal devices inserted at each end of the filter to draw the baskets apart and fracture the compression unit. The end sections of the arms are formed to lie in substantially parallel relationship to the vessel wall and the tips are inclined inwardly to preclude vessel wall penetration. If a device of this type is withdrawn before the endothelium layer grows over the arms, vessel wall damage is minimized. However, after growth of the endothelium layer the combined inward and longitudinal movement of the filter sections as they are drawn apart can tear this layer. U.S. Pat. No. 5,370,657 to Irie is illustrative of a prior art removable filter of this type which requires two removal devices.

SUMMARY OF THE INVENTION

It is a primary object of the present invention to provide a vessel implantable filter of shape memory material having temperature induced austenitic and martensite states which maybe easily removed by a single removal device after an extended period of time without significantly injuring the vessel wall.

Another object of the present invention is to provide a blood clot filter of shape memory material which operates in a temperature induced austenitic state to exert a force on the wall of a vessel by means of oppositely disposed legs to maintain the filter in place, but which may easily be removed after the endothelium layer has covered the ends of the filter legs without significant damage to the vessel wall.

A further object of the present invention is to provide a novel and improved vessel implantable filter having a group of arms and a group of legs which incline from a central axis. The ends of the arms in the group of arms are oriented to engage a vessel wall to orient and center the filter in the vessel, and the ends of the legs of the group of legs are oriented to engage the vessel wall to prevent longitudinal movement of the filter along the vessel. The ends of at least some of the legs are provided with hooks configured to be more elastic than the legs to permit the hooks to straighten in response to a withdrawal force to facilitate withdrawal from the endothelium layer without risk of significant injury to the vessel wall. In some cases, similar hooks can be formed on the ends of at least some of the arms.

Yet another object of the present invention is to provide a novel and improved vessel implantable filter having one or more expandable appendages which engage the wall of the vessel. An elastic hook is formed on the free end of an appendage to pierce the vessel wall and insure that the filter does not migrate in response to normal respiratory functions or in the event of a massive pulmonary embolism. The hook is formed to have a maximum migration force, and when subjected to forces below the maximum migration force, the hook retains its shape. When subjected to forces above the maximum migration force, the hook straightens and can be withdrawn without significant damage to the vessel wall.

A further object of the present invention is to provide a novel and improved vessel implantable filter having a plurality of expandable appendages which engage the wall of a vessel. Three to twelve of such appendages are provided which have an elastic hook formed on the free end of the appendage to pierce the vessel wall and insure that the filter does not migrate when subjected to a pressure gradient falling within a range of from 10 mmHg to 120 mmHg in a 28 mm vessel (filter migration resistance). Each hook is formed to have a maximum migration force, and when subjected to forces below the maximum migration force, the hook retains its shape. When subjected to forces above the maximum migration force, the hook straightens and can be withdrawn without significant damage to the vessel wall. The maximum migration force for each hook is dependent upon the desired total filter migration resistance and the number of hooks formed on the filter.

A still further object of the present invention is to provide a novel and improved removable embolus blood clot filter and filter delivery unit designed to insure delivery of the filter in a centered orientation to a precise location within a vessel. The filter delivery unit includes an elongate pusher wire of shape memory material having temperature induced austenitic and martensite states, with a handle at one end and a filter engaging spline at the opposite end. Spaced inwardly from the spline is a pusher pad which is longitudinally slotted to receive the elongate appendages of the filter. The pusher wire is reduced in diameter between the spline and pusher pad at a point adjacent to the pusher pad to impart a directional hinge to the pusher wire at the reduced portion.

According to the invention, a resilient blood clot filter is inwardly radially collapsible toward its longitudinal axis into a collapsed configuration for insertion into a body vessel, but is adapted for automatic radial expansion into contact with the inner wall of the vessel at two longitudinally spaced peripheral locations therein. The filter has leading and trailing ends and comprises a plurality of wires. The wires, in the normal expanded configuration of the filter, are in the form of a plurality of elongated arms and legs with openings between the wires to provide filter baskets opening at the leading end of the filter. The wires have peripheral portions for contact with the inner wall of the vein at two longitudinally spaced peripheral locations. The arms operate to center the filter while the legs terminate in hooks which anchor the filter but which straighten in response to force applied at the trailing end of the filter to facilitate removal of the filter.

To provide a filter that is inwardly radially collapsible from its normally expanded configuration toward its longitudinal axis into a collapsed configuration for insertion into a body vessel, the blood clot filter is preferably formed from a plurality of wire portions composed of a thermal shape memory material having a first, low-temperature condition and a second, high-temperature condition. The material in its low-temperature condition is relatively pliable (so that the wire portions may be straightened) and in its high-temperature condition is resiliently deformable and relatively rigid, and takes a predetermined functional form.

In the high-temperature condition of the material, the filter comprises coaxial first and second filter baskets, each filter basket being generally symmetrical about the longitudinal axis of the filter with both filter baskets being concave relative to the filter leading end.

BRIEF DESCRIPTIONS OF THE DRAWINGS

DETAILED DESCRIPTION

By forming the body of a blood clot filter of a Nitinol alloy material, such as Nitinol wire, transition between the martensitic and austenitic states of the material can be achieved by temperature transitions above and below a transition temperature or transition temperature range which is at or below body temperature. Such controlled temperature transitions have conventionally been employed to soften and contract the Nitinol filter body to facilitate insertion into a catheter and to subsequently expand and rigidify the body within a vascular or other passageway. Although the filters of the present invention are preferably formed from a temperature responsive shape memory material, such as Nitinol, they can also be formed of a compressible spring metal such as stainless steel or a suitable plastic.

Figure 1:
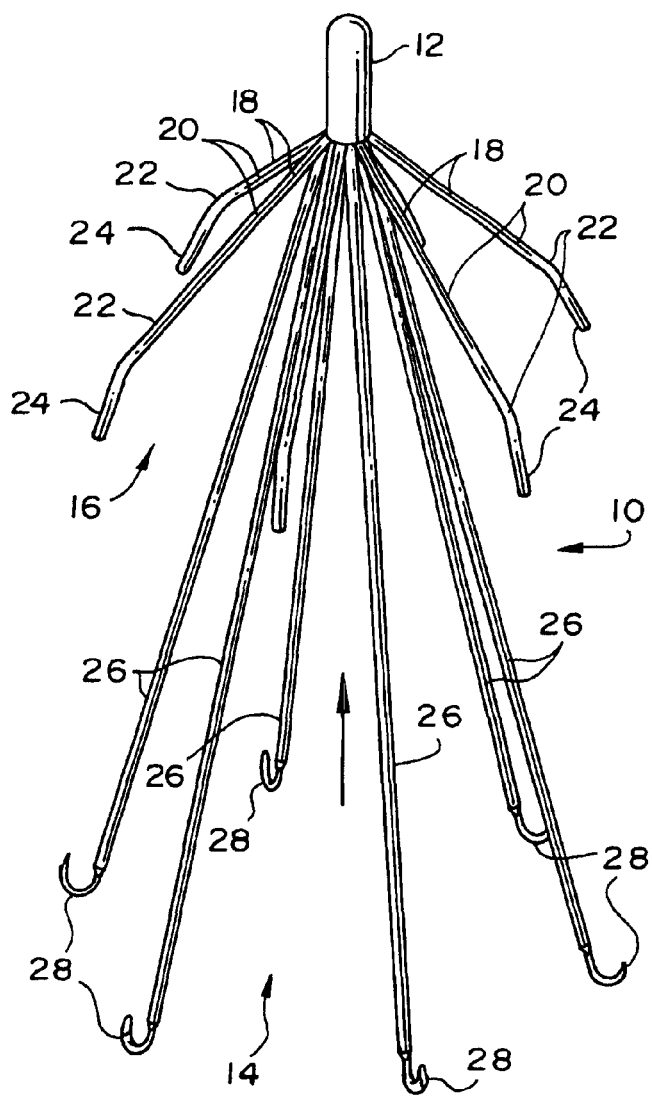
FIG. 1 is a view in side elevation of an expanded blood clot filter of the present invention.

Referring now to FIG. 1, an expanded blood clot filter 10 is illustrated which is made from sets of elongate metal wires. The wires are held together at the filter trailing end by a hub 12 where they are plasma welded together and to the hub or otherwise joined. In the low temperature martensite phase of wires made of thermal shape memory material, the sets of wires can be straightened and held in a straight form that can pass through a length of fine plastic tubing with an internal diameter of approximately 2 mm (#8 French catheter). In its high temperature austenitic form, the filter 10 recovers a preformed filtering shape as illustrated by FIG. 1. Similarly, wires of spring metal can be straightened and compressed within a catheter or tube and will diverge into the filter shape of FIG. 1 when the tube is removed.

In its normal expanded configuration or preformed filtering shape, filter 10 is a double filter, having a first forwardly disposed filter basket section 14 at the forward or leading end of the filter and a second forwardly disposed filter basket section 16. The two filter basket sections provide peripheral portions which can both engage the inner wall of a body vessel 17 at two longitudinally spaced locations, and the two filter basket sections are generally symmetrical about a longitudinal axis passing through the hub 12. On the other hand, the second forwardly disposed filter basket section 16, which is primarily a centering unit, may not always touch the vessel wall on all sides.

The second filter basket section 16 is formed from short lengths of wire which form arms 18 that extend angularly, outwardly and then downwardly from the hub 12 toward the forward end of the filter 10. Each arm 18 has a first arm section 20 which extends angularly outwardly from the hub 12 to a shoulder 22, and an outer arm section 24 extends angularly from the shoulder toward the forward end of the filter. The outer arm sections 24 are substantially straight lengths with ends which lie on a circle at their maximum divergence and engage the wall of a vessel at a slight angle (preferably within a range of from ten to forty-five degrees) to center the hub 12 within the vessel. For a filter which is to be removed by grasping the hub 12, it is important for the hub to be centered. Normally, there are six wires 18 of equal length extending radially outward from the hub 12 and circumferentially spaced, such as for example by sixty degrees of arc.

Figure 4:
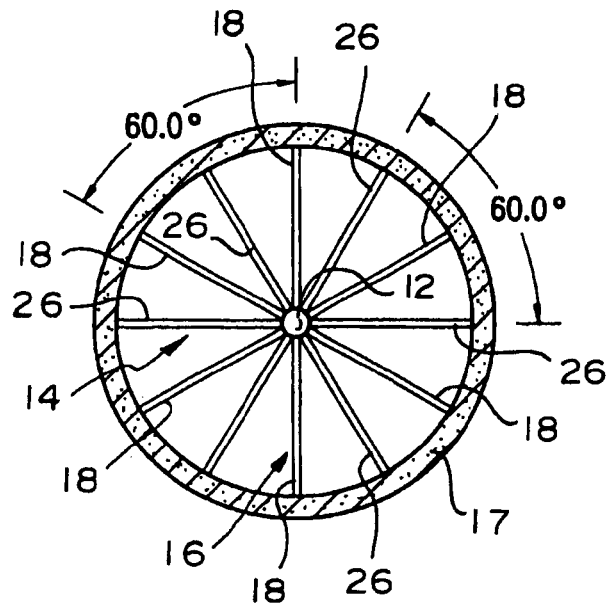
FIG. 4 is a cross sectional view of the blood clot filter of the present invention in place in a blood vessel.
Figure 7:
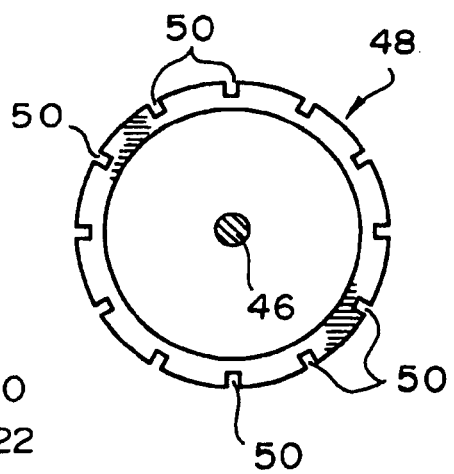
FIG. 7 is an enlarged view in end elevation of the pusher pad for the filter delivery unit of FIG. 6.

The first filter basket section 14 is the primary filter and can include up to twelve circumferentially spaced straight wires 26 forming downwardly extending legs which tilt outwardly of the longitudinal axis of the filter 10 from the hub 12. Six of the wires 26 are shown in FIG. 1, and may be of equal length, but normally they are not so that hooks 28 at the ends of the wires will fit within a catheter without becoming interconnected. The wires 26 are preferably much longer than the wires 18, and have tip sections which are uniquely formed, outwardly oriented hooks 28 which lie on a circle at the maximum divergence of the wires 26. There may be from three to twelve of the wires 26 formed with hooks 28, although in some instances, the wire arms 18 may include similarly formed hooks at the free ends thereof. The wires 26, in their expanded configuration of FIG. 1, are at a slight angle to the vessel wall, preferably within a range of from ten to forty-five degrees, while the hooks 28 penetrate the vessel wall to anchor the filter against movement. The wires 26 are radially offset relative to the wires 18 and may be positioned halfway between the wires 18 and also may be circumferentially spaced by sixty degrees of arc as shown in FIG. 4. Thus the combined filter basket sections 14 and 16 can provide a wire positioned at every thirty degrees of arc at the maximum divergence of the filter sections. With reference to the direction of blood flow shown by the arrow in FIG. 1, the filter section 14 forms a concave filter basket opening toward the leading end of the filter 10 while the filter section 16 forms a concave filter basket opening toward the leading end of the filter 10 downstream of the filter section 14.

The structure of the hooks 28 is important. As in the case of hooks formed on the legs of previously known permanent vena cava filters, these hooks 28 penetrate the vessel wall when the filter 10 is expanded to anchor the filter in place and prevent filter migration longitudinally of the vessel in either direction. However, when these hooks are implanted and subsequently covered by the endothelium layer, they and the filter can be withdrawn without risk of significant injury or rupture to the vena cava. Minor injury to the vessel wall due to hook withdrawal such as damage to the endothelial layer or local vena cava wall puncture is acceptable. However, previous filters with rigid anchoring hooks could not be withdrawn without causing unacceptable vessel tearing or local hemorrhage.

Figure 2:
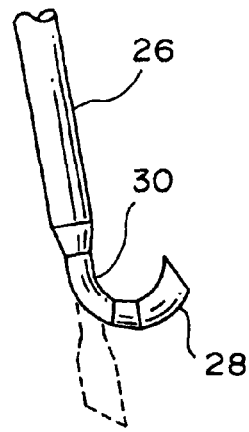
FIG. 2 is a view in side elevation of a hook for a leg of the filter of FIG. 1.

With reference to FIGS. 1 and 2, each hook 28 is provided with a juncture section 30 between the curvature of the hook and the leg 26 (or arm 18) to which the hook is attached. This juncture section is considerably reduced in cross section relative to the cross section of the leg 26 (or arm 18) and the remainder of the hook. The juncture section is sized such that it is of sufficient stiffness when the legs 26 (or arms 18) are expanded to permit the hook 28 to penetrate the vena cava wall. However, when the hook is to be withdrawn from the vessel wall, withdrawal force to which the hook is subjected will cause flexure in the juncture section 30 so that the hook moves toward a position parallel with the axis of the leg 26 (or arm 18) as shown in broken lines in FIG. 2. With the hook so straightened, it can be withdrawn without tearing the vessel wall leaving only a small puncture.

Figure 3:
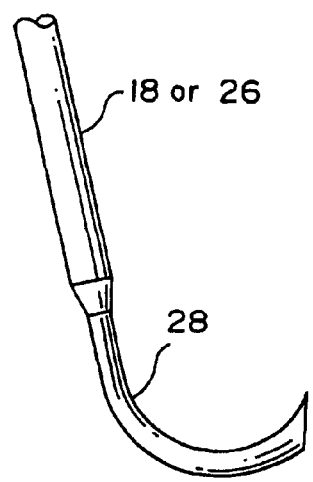
FIG. 3 is a view in side elevation of a second embodiment of a hook for a leg of the filter of FIG. 1.

With reference to FIG. 3, it will be noted that the entire hook 28 can be formed with a cross section throughout its length which is less than that of the leg 26 (or arm 18). This results in straightening of the hook over its entire length in response to a withdrawal force. This elasticity in the hook structure prevents the hook from tearing the vessel wall during withdrawal.

As previously indicated, while it is possible that the filter could be made from ductile metal alloys such as stainless steel, titanium, or elgiloy, it is preferable to make it from nitinol. Nitinol is a low modulus material which allows the arms and legs of the device to be designed to have low contact forces and pressures while still achieving sufficient anchoring strength to resist migration of the device. The force required to cause opening of the hooks 28 can be modulated to the total force required to resist filter migration. This is accomplished by changing the cross sectional area or geometry of the hooks, or by material selection.

In addition to temperature sensitivity, nitinol, when in the temperature induced austenitic state, is also subject to stress sensitivity which can cause the material to undergo a phase transformation from the austenitic to the martensitic state while the temperature of the material remains above the transition temperature level. By reducing a portion or all of the cross sectional area of the hooks 28 relative to that of the legs 26 (or arms 18), stress is concentrated in the areas of reduced cross section when longitudinal force is applied to the hub 12 in the direction of the trailing end of the filter to remove the filter, and the hooks become elastic and straighten. Thus the hooks, whether formed of nitinol, spring metal or plastic, are designed to bend toward a more straight configuration when a specific hook migration force is applied and spring back to their original shape once the hook migration force has been removed. The force or stress which is required to deform the hook can be correlated to the force applied to each hook of the device when it is fully occluded and the blood pressure in the vessel is allowed to reach 50 mmHg. This force is approximately 70 gms on each leg of a six leg device for 50 mmHg. pressure differential in a 28 mm vessel. The desired total migration resistance force for the filter is desirably 420 gms, and more legs 26 with hooks 28 can be added to lower maximum migration force for each hook. The load on the filter would be correspondingly smaller in vessels of smaller diameter. The object is to have the hook perform as an anchoring mechanism at a predetermined filter migration resistance force within a range of 10 mmHg up to 120 mmHg. Having maintained its geometry at a predetermined filter migration resistance force within this range, the hook should begin to deform in response to a higher force applied in the direction of the filter trailing end and release at a force substantially less than that which would cause damage to the vessel tissue. It is the ability of the hook to straighten somewhat that allows for safe removal of the device from the vessel wall.

After the filter 10 has remained in place within a vessel for a period of time in excess of two weeks, the endothelium layer will grow over the hooks 28. However, since these hooks, when subjected to a withdrawal force become substantially straight sections of wire oriented at a small angle to the vessel wall, the filter can be removed leaving only six pin point lesions in the surface of the endothelium. To accomplish this, a catheter or similar tubular unit is inserted over the hub 12 and into engagement with the arms 18. While the hub 12 is held stationary, the catheter is moved downwardly forcing the arms 18 downwardly, and subsequently the arms 26 are engaged and forced downwardly thereby withdrawing the hooks 28 from the endothelium layer. Then the hub 12 is drawn into the catheter to collapse the entire filter 10 within the catheter. When the filter is formed from shape memory material, cooling fluid can be passed through the catheter to aid in collapsing the filter.

The primary objective of the hooks 28 is to ensure that the filter does not migrate during normal respiratory function or in the event of a massive pulmonary embolism. Normal inferior vena cava (IVC) pressures are between 2-5 mmHg. An occluded IVC can potentially pressurize to 35 mmHg below the occlusion. To ensure filter stability, a 50 mmHg pressure drop across the filter may therefore be chosen as the design criteria for the filter migration resistance force for the removable filter 10. When a removal pressure is applied to the filter that is greater than 50 mmHg, the hooks 28 will deform and release from the vessel wall. The pressure required to deform the hooks an be converted to force by the following calculations.

Since 51.76 mm Hg=1.0 pounds per square inch (psi)
50 mm Hg=0.9668 psi
For a 28 mm vena cava $$A = \frac{\pi}{4} (28)^2 \text{ mm}^2 = 615.4 \text{ mm}^2 = 0.9539 \text{ inches}^2$$

Migration force is calculated by:

$$P = \frac{F}{A} \qquad F = P \times A$$

$$0.9668 \text{ psi} \times 0.9539 \text{ inches}^2 = 0.9223 \text{ pounds} = 418.7 \text{ grams}$$

It is important to recognize that as vena cava diameter increases so does the force required to resist 50 mmHg of pressure.

Depending on the number of filter hooks, the strength of each can be calculated. For a device that has six hooks:

$$\text{Hook Strength} = \frac{\text{Filter Migration Resistance Force}}{\text{Number of Hooks}}$$
$$= \frac{418.7}{6}$$
$$= 69.7 \text{ grams}$$

Each hook must be capable of resisting approximately 70 grams of force for the filter 10 to resist 50 mmHg pressure gradient in a 28 mm vessel.

To prevent excessive vessel trauma the individual hook needs to be relatively weak. By balancing the number hooks and the individual hook strength, minimal vessel injury can be achieved while still maintaining the 50 mmHg pressure gradient criteria, or some other predetermined pressure gradient criteria within a range of from 10 mmHg to 120 mmHg.

Figure 5:
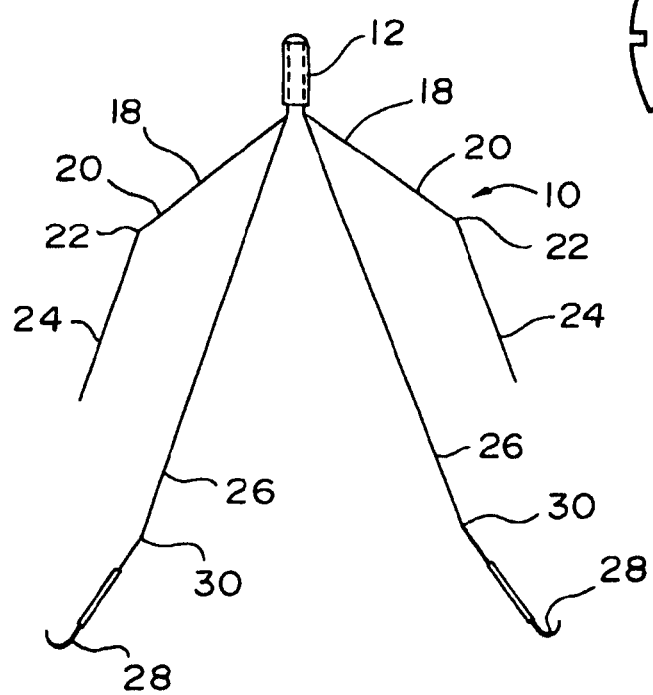
FIG. 5 is a diagrammatic view of a second embodiment of the leg structure for the blood clot filter of the present invention.
Figure 6:
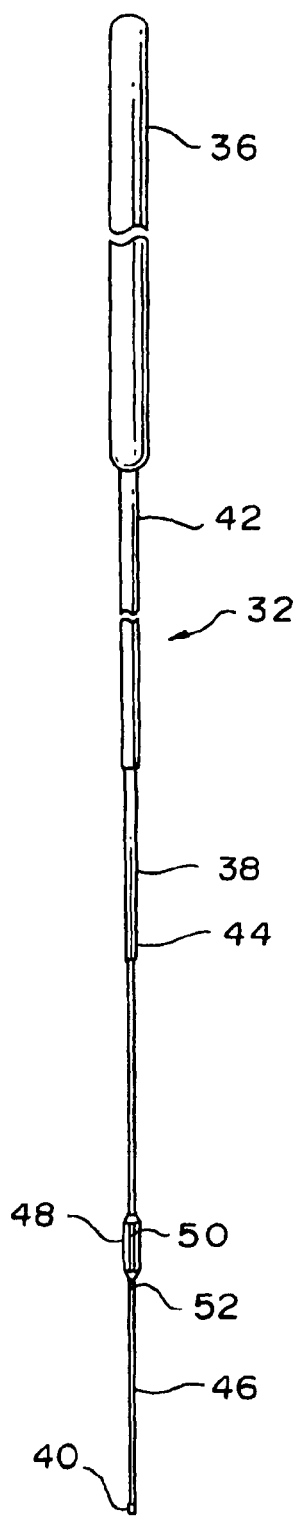
FIG. 6 is a plan view of the filter delivery unit of the present invention.

Referring to FIG. 5, the legs 26 may be angled outwardly from a shoulder 30 adjacent to but spaced from the outer end of each leg. When the legs are released from compression in a catheter or other tube into a body vessel, this bend in each leg insures that the hooks 28 are, in effect, spring loaded in the tube and that they will not cross as they are deployed from the tube. Since the legs angle outwardly from the shoulders 30, the hooks 28 are rapidly deployed outwardly as the insertion tube is withdrawn.

The filter delivery unit 32 is adapted to deliver the filter 10 through a catheter or delivery tube 34 to a precise, centered position within a body vessel. The filter delivery unit includes a handle 36 at one end, and an elongate pusher wire 38 extends outwardly from the handle 36. At the free end of the pusher wire is an enlarged filter engaging pusher pad 40.

The elongate pusher wire 38 is preferably formed of superelastic material and may be formed of thermally responsive shape memory material, such as nitinol. The pusher wire includes sections 42, 44 and 46 which progressively decrease in cross section beginning at the handle 36. The temperature transformation level of the pusher wire is such that when the wire is encased in a catheter or delivery tube, it remains in a martensitic state and is therefore somewhat pliable and flexible so that it can conform to curvatures in a catheter or delivery tube which passes through a body vessel. As the delivery tube is withdrawn, body temperature causes the exposed portions of the pusher wire to assume the move rigid austenitic state for filter positioning.

Figure 8:
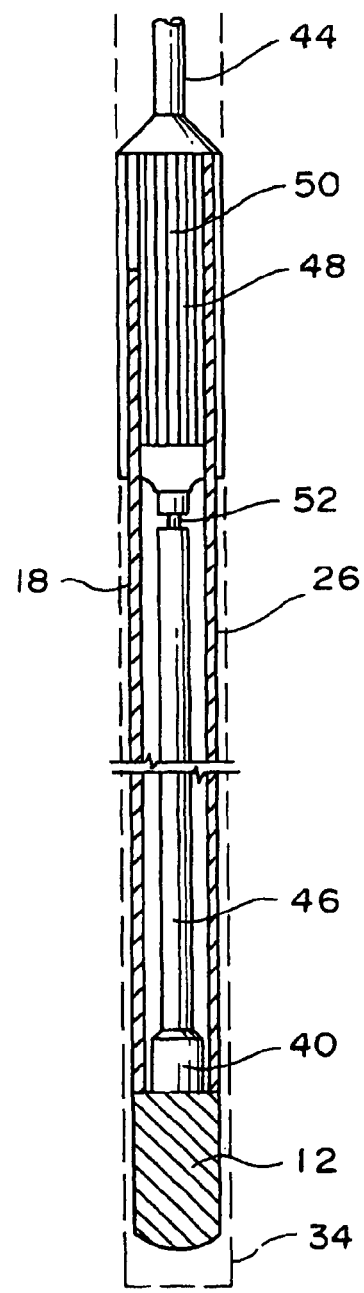
FIG. 8 is an enlarged view of the end section of the filter delivery unit of FIG. 6 in engagement with a filter.

A slotted spline 48 is secured to the pusher wire 38 between the sections 44 and 46. The pusher pad is provided with a plurality of spaced, peripherally arranged, longitudinally extending grooves 50 of sufficient number to individually receive the legs 26 of a filter 10. The spline is spaced from the pusher pad 40 for a distance less than the length of the filter legs 26 so that the legs can be received in the grooves 50 when the pusher pad engages the filter hub 12 as shown in FIG. 8. It will be noted that the pusher wire section 46 is reduced in cross section at 52 adjacent to the spline 48.

To load the filter delivery unit 32 to insert a filter 10 into a body vessel, the pusher wire section 46 is inserted from the leading end of the filter 10 under the arms 18 and legs 26 until the pusher pad 40 engages the underside of the hub 12 at the apex of the filter as shown in FIG. 8. Then the legs 26 of the filter, two being shown for purposes of illustration in FIG. 8, are inserted into the grooves 50 in the spline, and the arms 18 are spirally wrapped around the spline. The pusher wire, with the filter in place, is inserted into a catheter or delivery tube 34. When the catheter or delivery tube with the filter 10 is at a desired location within a body vessel, it is removed from around the delivery unit and filter to expose the filter. First the hub 12 of the filter is exposed and then the pusher wire section 46 emerges. When the pusher wire is formed of thermal shape memory material, the emergence of wire section 46 causes this section, with the exception of the portion of reduced cross section 52, to transform to the austenitic state and to become more rigid. As the filter pad 48 emerges, the centering arms 18 of the filter 10 are exposed and released and transform to the austenitic state to achieve radial expansion outwardly toward the vessel wall. If the filter is not centered in the vessel, some of the arms 18 will engage the vessel wall and apply stress to the reduced cross section portion 52 of the pusher wire section 46. Stress causes this portion 52 to remain in the flexible martensitic state, and the pusher wire section 46 will pivot at the portion 52 to permit radial movement of the spline 40 in all directions to aid the arms 18 in centering the filter 10 within the vessel. Thus the portion 52 provides a directional hinge for centering the filter.

With the filter centered, the legs 26 are exposed and expand radially to engage the vessel wall and anchor the filter against migration. The pusher wire and catheter or delivery tube are now withdrawn from the body vessel.

When the pusher wire is formed of flexible material which is not a thermal, shape memory material, the reduced cross sectional portion 52 to the pusher wire section 46 has greater flexibility than the remainder of the pusher wire and thus forms a flexible, directional hinge to aid in centering the filter in the manner previously described.

The invention claimed is:

1. A method of recovering a blood filter implanted in a blood vessel, the blood filter having a plurality of legs that extend from a hub and radially spaced about a longitudinal axis, each of the legs having a hook coupled to a wall of the blood vessel, the hook having a curved profile, the method comprising:

deforming the hook of each of the legs from the curved profile towards a generally straight profile by applying a force greater than 70 grams to each leg in a direction along the longitudinal axis towards the hub to separate the hook of the blood filter from the wall of the blood vessel, the hook having an elasticity greater than an elasticity of its corresponding leg; and forcing the plurality of legs to move towards the longitudinal axis.

2. The method of claim 1, wherein the applying comprises applying a force greater than 420 grams to the hub to separate the hooks of the blood filter from the wall of the blood vessel of about 28 millimeters.

3. The method of claim 2, wherein the deforming comprises bending each of the hooks toward a generally straight configuration to release a tip of the hook from the blood vessel wall.

* * * * *